United States Patent
Timmerman et al.

[11] Patent Number: 5,714,501
[45] Date of Patent: Feb. 3, 1998

[54] PIPERIDINE DERIVATIVES

[75] Inventors: Henk Timmerman, Voorschoten; Mingqiang Zhang, Amstelveen, both of Netherlands

[73] Assignee: Kowa Co., Ltd., Nagoya, Japan

[21] Appl. No.: 634,427

[22] Filed: Apr. 18, 1996

[30] Foreign Application Priority Data

Apr. 24, 1995 [JP] Japan ................... 7-098797

[51] Int. Cl.⁶ ............ A61K 3/445; C07D 211/20
[52] U.S. Cl. ............ 514/325; 514/290; 546/93; 546/203
[58] Field of Search .............. 514/325, 290; 546/203, 93

[56] References Cited

U.S. PATENT DOCUMENTS

| | | | |
|---|---|---|---|
| 4,282,233 | 8/1981 | Vilani | 514/290 |
| 4,356,184 | 10/1982 | Deason | 514/277 |
| 4,863,931 | 9/1989 | Schumacher | 514/290 |
| 5,151,423 | 9/1992 | Piwinski et al. | 514/254 |
| 5,464,840 | 11/1995 | Ting et al. | 514/277 |
| 5,508,280 | 4/1996 | Hibert et al. | 514/255 |

Primary Examiner—Ceila Chang
Attorney, Agent, or Firm—Oblon, Spivak, McClelland, Maier & Neustadt, P.C.

[57] ABSTRACT

A piperidine derivative of formula (1) or salts thereof:

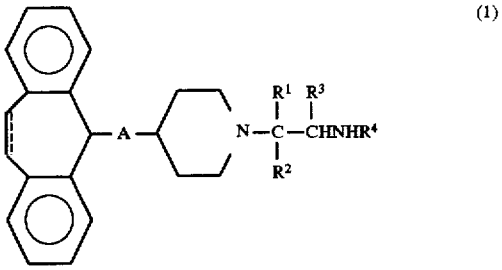

wherein $R^1$ and $R^2$ independently represent H or together represent O, $R^3$ represents H, —$R^5$—COOR⁶, or —COOR⁶ (wherein $R^5$ is a lower alkylene group, —CONH—, or —CONHCH$_2$, and $R^6$ is H or a lower alkyl group), $R^4$ represents H, an aralkyloxy carbonyl group, an aminomethyl carbonyl group, or an aralkyloxy carbonyl aminomethyl carbonyl group. A represents O or a double bond, and the broken line has the meaning that a bonding hand may be present; and preventive and therapeutic agents for allergies, antihistaminic agents, and antileucotriene agents comprising the derivative or salts as their effective component.

The compound of formula (1) has excellent antihistaminic activities and antileukotriene activities, which are well balanced, and is useful as a drug for the prevention and treatment of allergies such as asthma, allergic rhinitis, allergic dermatosis and urticaria.

7 Claims, No Drawings

PIPERIDINE DERIVATIVES

TECHNICAL FIELD

The present invention relates to a piperidine derivative and salts thereof, which have excellent antihistaminic activity and antileukotriene activity, and are useful as a drug for the prevention and treatment of various allergic diseases.

TECHNICAL BACKGROUND

Histamine exhibits various physiological activities as a result of interaction with specific receptors in the membranes of cell surfaces. By the mediation of $H_1$-receptors, histamine stimulates smooth muscles such as those in the bronchi to contract. Contraction of the bronchi leads to limited amounts of air to pass into and out of the lungs as in asthma. Histamine also elevates the permeability of the capillary walls so that increased amounts of the blood constituents escape into the tissue space, causing an increase in the flow of lymph and its protein content to form edema. Antihistamine drugs have been proved to be successful for the treatment of many allergies, e.g., allergic rhinitis, allergic dermatosis, urticaria, etc. However for the treatment of some severe allergies such as asthma, it has been found that histamine $H_1$-receptor antagonists are less effective.

Leukotrienes are a group of arachidonic acid metabolites which are collectively long known as slow-reacting substances of anaphylaxis (SRS-A). The physiological action of leukotrienes include bronchoconstriction, mucus hypersecretion and pulmonary edema which all contribute to airway obstruction characteristic of asthma. Leukotrienes also attract leukocytes to sites of cellular injury and thus affect the mechanism of inflammation. In contrast to histamine, leukotrienes induce prolonged bronchoconstriction. Clinical trials of the compounds known to act as antagonists to leukotriene $D_4$ ($LTD_4$) receptors have shown that these compounds are effective for the treatment of asthma [Manning, P. J. et al: N. Engl. J. Med. 1990, 323, 1736–1739 and Taylor, I. K. et al: Lancet 1991, 337, 690–694].

Accordingly, compounds having antagonizing activities on both histamine $H_1$-receptors and leukotriene receptors are potentially useful therapeutics for the prevention and treatment of allergic diseases in general and asthma in particular.

Many tricyclic compounds have been known to possess either histamine $H_1$-receptor antagonism or leukotriene $D_4$ receptor antagonism (Japanese Patent Application Laid-open (kokai) No. 5-239,002, Japanese Patent Application Laid-open (kokai) No. 6-116,273, Spanish Patent Publication No. 2,042,421, and PCT patent publication No. 9,419, 345).

However, these compounds do not exhibit an equal level of antagonism to histamine $H_1$-receptors and leukotriene $D_4$ receptors. Therefore, they fail to provide satisfactory therapeutic effects for the treatment of severe allergies such as asthma.

It is also known that several new $H_1$-antagonists, such as terfenadine and astemizole, may cause cardiotoxicity, especially when applied in high doses or concomitantly with other drugs which inhibit their metabolism.

Accordingly, an object of the present invention is to provide a compound which has anti-histaminic activities and anti-leukotriene activities, which provides satisfactory therapeutic effects, which does not migrate to the central nerve system and are therefore devoid of sedating side effects, which also exhibits no or much less other adverse side effects such as those in cardiovascular system, and which is thus useful as a preventive and therapeutic agent for asthma, allergic rhinitis, allergic dermatosis, and urticaria and other types of allergic and inflammatory diseases.

DISCLOSURE OF THE INVENTION

Under the above circumstances, the present inventors synthesized numerous piperidine derivatives and investigated their pharmacological activities. As a result, they found that the compounds of the following formula (1) possess excellent antihistaminic activities, antileukotriene activities, and antiallergic activities with suppressed migration to the central nerve system, therefore exhibiting no adverse side effects such as central nerve system depression, and that they are useful as preventive and therapeutic agents for allergies such as asthma, leading to completion of the invention.

Accordingly, the present invention provides a piperidine derivative of formula (1) or a salt thereof:

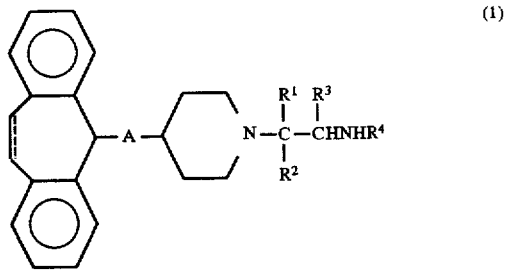

wherein $R^1$ and $R^2$ independently represent a hydrogen atom or they link to represent an oxygen atom together, $R^3$ represents a hydrogen atom, $-R^5-COOR^6$, or $-COOR^6$ (wherein $R^5$ is a lower alkylene group, $-CONH-$, or $-CONHCH_2$, and $R^6$ is a hydrogen atom or a lower alkyl group), $R^4$ represents a hydrogen atom, an aralkyloxy carbonyl group, an aminomethyl carbonyl group, or an aralkyloxy carbonyl aminomethyl carbonyl group, A represents an oxygen atom or a double bond, and the broken line has the meaning that a bonding hand may be present.

The present invention also provides antihistaminic agents, antileukotriene agents, and antiallergic agents comprising the piperidine derivative of the above-described formula (1) as their effective component.

The present invention further provides pharmaceutical compositions comprising the piperidine derivative as defined above or a salt thereof and a pharmaceutically acceptable carrier.

The present invention further provides use of the piperidine derivative as a medicine.

The present invention further provides a method for treating allergic diseases, comprising administering an effective amount of the peperidine derivative as defined above or a salt thereof.

BEST MODE FOR CARRYING OUT THE INVENTION

In the present invention, examples of the lower alkylene group includes C1–C5 straight or branched alkylene groups, of which C1–C4 linear or branched alkylene groups are preferred. The alkylene groups are preferably methylene, ethylene, trimethylene, tetramethylene, and propylene. In particular, methylene and ethylene are preferred.

Examples of the lower alkyl groups include C1–C5 linear or branched alkyl groups, of which C1–C4 linear or branched alkyl groups are preferred. The alkyl groups are preferably methyl, ethyl, n-propyl, n-butyl, isopropyl, and tert-butyl. In particular, methyl and ethyl are preferred.

Examples of the aralkyl group include phenyl $C_{1-4}$ alkyl, naphthyl $C_{1-4}$ alkyl, and biphenylmethyl, of which phenyl $C_{1-4}$ alkyl is preferred, and benzyl is particularly preferred.

The compounds of the present invention represented by formula (1) can be present in the form of a solvate typified by a hydrate, and therefore, solvates of the compounds are within the scope of the present invention. Moreover, the present compounds (1) have stereochemical isomers attributed to asymmetric carbon atoms, and these stereochemical isomers either optically pure or as racemic mixtures are also encompassed by the present invention.

No particular limitation is imposed on the salts of the compounds represented by formula (1) as long as they are pharmacologically acceptable. Examples of such salts include acid adducts of mineral acids, such as hydrochlorides, hydrobromides, hydroiodides, sulfates and phosphates; acid adducts of organic acids, such as benzoates, methanesulfonates, ethanesulfonates, benzenesulfonates, p-toluenesulfonates, oxalates, maleates, fumarates, tartarates and citrates; and metal salts such as sodium salts, potassium salts, calcium salts, magnesium salts, manganese salts, iron salts and aluminum salts.

The present compounds (1) and their salts are prepared, for example, by the following reaction scheme:

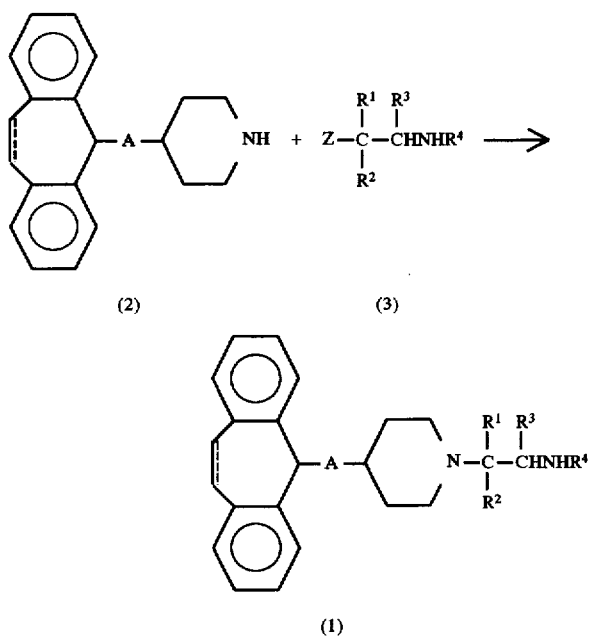

wherein Z is an atom or a group which can be eliminated, such as a halogen atom, a methane sulfonyloxy group, and a paratoluene sulfonyloxy group, and $R^1$, $R^2$, $R^3$, $R^4$, A, and the broken line have the same meaning as defined above.

In other words, the present compound (1) can be obtained by reacting compound (2) with compound (3), and if necessary, hydrolyzing or esterifying the resulting product or converting the resulting product into an amide.

The compound (2) used in this reaction scheme can be prepared, for example, according to the methods described in the following publications: E. L. Engelhardt et. al., J. Med. Chem., 1965, 8, 829–835 and C van der Stelt et al., Arzneim.-Forsch., 1966, 16, 1342. Moreover, compound (3) used in the above reaction scheme can be prepared, for example, according to the methods described in the following publications: N. Tamura et al., Tetrahedron, 1988, 44, 3231–3240; R. A. Boissonnas et al., Helv. Chim. Acta, 1955, 38, 1491–1501; M. Goodman et al., J. Am. Chem. Soc. 1962, 84, 1279–1283; and M. Bergman et al., Ber. 1932, 65, 1192–1201.

The reaction of compound (2) and compound (3) is preferably carried out in the presence of a base. Examples of suitable bases include tertiary amines such as triethylamine, tributylamine, pyridine, picoline, lutidine and collidine; metal alkoxides such as sodium methoxide and sodium ethoxide; inorganic bases such as potassium carbonate, sodium carbonate and sodium hydrogencarbonate. Examples of suitable reaction solvents include aromatic hydrocarbons such as benzene and toluene; ethers such as tetrahydrofuran and dioxane; non-polar organic solvents such as acetone and acetonitrile; alcohols such as methanol, ethanol, isopropanol and n-butanol; polar organic solvents such as dimethylsulfoxide and N,N-dimethylformamide. The reaction normally proceeds at room temperature or under heating.

After completion of the reaction, a suitable treatment of the obtained compound according to a conventional manner will provide the target compound of the present invention, which may further be purified by an ordinary purification process such as recrystallization, column chromatography, etc., as desired. If necessary, the compound may be converted into the aforementioned salts by a method known per se.

The thus-obtained compounds (1) and their salts of the present invention exhibit excellent antihistaminic activity and excellent antileukotriene $D_4$ activity as shown in the Examples below, and therefore, they are very useful in the prevention and treatment of various allergies of the human and animals.

Examples of the manner of administration of the present compounds as a drug for preventing or treating allergies include oral administrations by way of tablets, capsules, granules, powders, and syrups and non-oral administrations such as intravenous injections, intramuscular injections, suppositories, inhalations, percutaneous absorptions, eye drops, and nasal drops. In order to prepare a medicine in the above mentioned various physical forms, pharmaceutically acceptable carriers known per se may further be employed in a suitable combination, which include excipients, bulking agents, binders, disintegrants, surfactants, lubricants, dispersing agents, buffering agents, preservatives, flavors, perfumes, coating agents, etc.

The dosage of the compound of the present invention for the prevention and treatment of allergic diseases varies depending on the age, weight, symptom, manner of administration, frequency of the administration, etc. In general, it is preferred that the compound of the present invention be administered to an adult in an amount of from about 1 to 1,000 mg/day at a time or as divided in several times, orally or non-orally.

EXAMPLES

The present invention will now be explained by way of examples, which however, should not be construed as limiting the invention thereto.

Example 1

Methyl (S)-2-benzyloxycarbonylamino-3-[4-(5H-dibenzo[a,d]-cyclohepten-5-ylidene)piperidin-1-yl]propionate A mixture of 4-(5H-dibenzo[a,d]cyclohepten-5-ylidene) piperidine (2.73 g, 10 mmol), L-methyl 2-benzyloxycarbonylamino-3-chloropropionate (2.71 g, 10 mmol), NaI(1.50 g, 10 mmol) and $Na_2CO_3$ (1.06 g, 10 mmol) in 250 ml dry acetone was refluxed overnight. After evaporating acetone, the residue was extracted with $CH_2Cl_2$. The $CH_2Cl_2$ solution was dried over $Na_2SO_4$ and evaporated to dryness. The resulting light brown oil was put on a silica gel column and eluated with ether. The title compound was thus obtained as a slightly yellow solid. Yield: 2.49 g (49%).

mp.116.0°–118.8° C.

$[\alpha]D^{25}$ –2.1°(c=1, $CHCl_3$).

$^1H$ NMR($CDCl_3$)δ(ppm): 2.0–2.7 (m, 10H, piperidine H+piperidine-NC$\underline{H_2}$CH), 3.6(s, 3H, $OCH_3$), 4.35 (m,1H, piperidine-NCH$_2$C$\underline{H}$), 5.1 (s, 2H, $OCH_2Ph$), 5.8 (d, 1H, J=6 Hz, NH), 6.9 (s, 2H, dibenzocyclohepten $C_{10,11}$—H), 7.15–7.4 (m, 13H, aromatic H).

Example 2

Methyl (S)-2-benzyloxycarbonylamino-3-[4-(10,11-dihydro-5H-dibenzo[a,d]cyclohepten-5-ylidene)piperidin-1-yl]propionate The title compound, a white crystalline, was prepared in a similar way as described under Example 1 with 4-(10,11-dihydro-5H-dibenzo[a,d]cyclohepten-5-ylidene)piperidine (2.75 g, 10 mmol) instead of 4-(5H-dibenzo[a,d] cyclohepten-5-ylidene) piperidine. Yield: 2.55 g (50%).

mp. 131.7°–132.3° C. (EtOH).

$[\alpha]D^{25}$ –0.5° (c=1, $CHCl_3$).

$^1H$ NMR($CDCl_3$)δ(ppm):2.3–2.7(m, 10H, piperidine H+piperidine-NC$\underline{H_2}$CH), 2.85 and 3.5 (two m, 4H, dibenzocyclohepten $C_{10,11}$—H), 3.75(s, 3H, $OCH_3$), 4.4(m, 1H, piperidine-NCH$_2$C$\underline{H}$), 5.15 (s, 2H, $OCH_2Ph$), 5.75 (d, 1H, J=6 Hz, NH), 7.1–7.4 (m, 13H, aromatic H.)

Example 3

Methyl (R)-2-benzyloxycarbonylamino-3-[4-(10,11-dihydro-5H-dibenzo[a,d]cyclohepten-5-ylidene)piperidin-1-yl]propionate The title compound, a white crystalline, was prepared in a similar way as described under Example 2 using D-methyl 2-benzyloxycarbonylamino-3-chloropropionate in the place of L-methyl 2-benzyloxy-carbonylamino-3-chloropropionate. Yield:54%.

mp. 135.7°–136.6]C.(EtOH).

$[\alpha]D^{25}$ +0.7°(c=1, $CHCl_3$).

$^1H$ NMR ($CDCl_3$)δ(ppm): identical to those of the title compound.

Example 4

Methyl (S)-2-benzyloxycarbonylamino-3-[4-(10,11-dihydro-5H-dibenzo[a,d]cyclohepten-5-yloxy)piperidin-1-yl]propionate The title compound, a light yellow oil, was prepared in a similar way as described under Example 1 with 4-(10,11-dihydro-5H-dibenzo[a,d]cyclohepten-5-yloxy)piperidine (2.93 g, 10 mmol) instead of 4-(5H-dibenzo[a,d] cyclohepten-5-ylidine)piperidine. Yield: 4.12 g (78%).

$[\alpha]D^{25}$ –1.5°(c=1, $CHCl_3$).

$^1H$ NMR($CDCl_3$)δ(ppm):1.75–2.65(m, 10H, piperidine H+piperidine-NC$\underline{H_2}$CH), 3.05 and 3.4 (two m, 4H, dibenzocyclohepten $C_{10,11}$—H), 3.55(m, 1H, piperidine $C_4$,—H), 3.65(s, 3H, $OCH_3$), 4.25(m, 1H, piperidine-NCH$_2$C$\underline{H}$), 5.05 (s, 2H, $OCH_2Ph$), 5.5(s, 1H, dibenzocyclohepten $C_5$—H), 5.6(d, 1H, J=6 Hz, NH), 7.1–7.4(m, 13H, aromatic H).

Example 5

Methyl (R)-2-benzyloxycarbonylamino-3-[4-(10,11-dihydro-5H-dibenzo[a,d]cyclohepten-5-yloxy)piperidin-1-yl]propionate The title compound, a slightly brown oil, was prepared in a similar way as described under Example 4 using D-methyl 2-benzyloxycarbonylamino-3-chloropropionate in the place of L-methyl 2-benzyloxycarbonylamino-3-chloropropionate. Yield:71%.

$[\alpha]D^{25}$ +1.5° (c=1, $CHCl_3$).

$^1H$ NMR($CDCl_3$)δ(ppm): identical to those of the title compound.

Example 6

(S)-2-Benzyloxycarbonylamino-3-[4-(5H-dibenzo[a,d] cyclohepten-5-ylidene)piperidin-1-yl]propionic acid To a solution of methyl (S)-2-benzyloxycarbonylamino-3-[4-(5H-dibenzo[a,d]cyclohepten-5-ylidene)piperidin-1-yl]propionate(2 g, 3.9 mmol) in 30 ml ethanol was added 10 ml of 1N NaOH aqueous solution. The mixture was then stirred at room temperature for 3 hours. After removing most ethanol under reduced pressure, the remaining mixture was diluted with ice-water and neutralized with acetic acid. The mixture was then extracted with chloroform (2×30 ml). The combined chloroform extract was washed with saline and dried over $Na_2SO_4$. After evaporating to dryness, the solid residue was recrystallized from ethanol to afford the title compound as a white crystalline. Yield:1.77 g (91%)

mp. 178.3°–179.4° C.

$[\alpha]D^{25}$ –26.3°(c=1, DMF).

$^1H$ NMR($CDCl_3$)δ(ppm):2.1–2.8(m, 10H, piperidine H+piperidine-NC$\underline{H_2}$CH), 4.3(m, 1H, piperidine-NCH$_2$C$\underline{H}$), 5.15(s, 2H, $OCH_2Ph$), 5.25(br s, 1H, NHCOO), 6.45(br s, 1H, piperidine-N$^+$H), 6.95(s, 2H, dibenzocyclohepten $C_{10,11}$—H), 7.2–7.4(m, 13H, aromatic H).

Example 7

(S)-2-Benzyloxycarbonylamino-3-[4-(10,11-dihydro-5H-dibenzo[a,d]cyclohepten-5-ylidene)-piperidin-1-yl] propionic acid The title compound, a white crystalline, was prepared in a similar way as described under Example 6 from methyl (S)-2-benzyloxycarbonylamino-3-[4-(10,11-dihydro-5H-dibenzo[a,d]cycrohepten-5-ylidene)piperidin-1-yl] propionate. Yield: 95%.

mp. 149.9°–152.3° C.(EtOH).

$[\alpha]D^{25}$ –28.6°(c=1, DMF).

$^1H$ NMR($CDCl_3$)δ(ppm):2.4–2.85(m, 10H, piperidine H+piperidine-NC$\underline{H_2}$CH), 2.9 and 3.4(two m, 4H, dibenzocyclohepten $C_{10,11}$—H), 4.15(m, 1H, piperidine-NCH$_2$ C$\underline{H}$), 4.9(br s, 1H, NHCOO), 5.05(s, 2H, $OCH_2Ph$), 6.4(br s, 1H, piperidine-N$^+$H), 6.9–7.15(m, 13H, aromatic H).

MS(m/z):496[M]$^+$ 387[M—H—$PhCH_2OH$]$^-$.

Example 8

(R)-2-Benzyloxycarbonylamino-3-[4-(10,11-dihydro-5H-dibenzo[a,d]-cyclohepten-5-ylidene)piperidin-1-yl] propionic acid The title compound, a white crystalline, was prepared in a similar way as described under Example 7 starting with methyl (R)-2-benzyloxycarbonylamino-3-[4-(10,11-dihydro-5H-dibenzo[a,d]cyclo-hepten-5-yl-idene) piperidine-1-yl]propionate. Yield:92%.

mp. 149.9°–152.3° C.(MeOH).

$[\alpha]D^{25}$ +28.5°(c=1, DMF).

$^1H$ NMR($CDCl_3$)δ(ppm):identical to those of the title compound.

Example 9

(S)-2-Benzyloxycarbonylamino-3-[4-(10,11-dihydro-5H-dibenzo[a,d]-cyclohepten-5-yloxy)piperidin-1-yl]propionic acid The title compound, a slightly yellow crystalline, was prepared in a similar way as described under Example 6 from methyl (S)-2-benzyloxycarbonylamino-3-[4-(10,11-dihydro-5H-dibenzo[a,d]cyclohepten-5-yl-oxy)piperidin-1-yl]propionate. Yield: 83%.

mp. 131.5°–133.0° C.(EtOH).

$[\alpha]D^{25}$–7.1°(c=1, DMF).

$^1$H NMR(CDCl$_3$)δ(ppm): 1.8–2.9(m, 10H, piperidine H+piperidine-NC$\underline{H}_2$CH), 3.05 and 3.5(two m, 5H, dibenzocyclohepten C$_{10,11}$—H+piperidine C$_4$,—H), 4.25(m, 1H, piperidine-NCH$_2$C$\underline{H}$), 4.95(s, 2H, OCH$_2$Ph), 5.35(br s, 1H, dibenzocyclohepten C$_5$—H), 5.7 (d,1H,J=5.3 Hz,NHCOO), 6.55(br s, 1H, piperidine-N$^+$H), 7.05–7.4(m, 13H, aromatic H).

MS(m/z):514[M]$^+$, 405[M—H—PhCH$_2$OH]$^-$, 208 [dibenzosuberone]$^-$.

Example 10

(R)-2-Benzyloxycarbonylamino-3-[4-(10,11-dihydro-5H-dibenzo[a,d]-cyclohepten-5-yloxy)piperidin-1-yl]propionic acid The title compound, a white crystalline, was prepared in a similar way as described under Example 9 starting with methyl (R)-2-benzyloycarbonylamino-3-[4-(10,11-dihydro-5H-dibenzo[a,d]-cyclohepten-5-yloxy)piperidin-1-yl] propionate. Yield: 85%.

mp. 128.0°–129.5° C. (MeOH/Et$_2$O).

$[\alpha]D^{25}$+7.8°(c=1, DMF).

$^1$H NMR(CDCl$_3$)δ(ppm): identical to those of the title compound.

Example 11

Ethyl α-{(S)-2-benzyloxycarbonylamino-3-[4-(5H-dibenzo[a,d]-cyclohepten-5-ylidene)piperidine-1-yl]propionylamino}acetate A solution of (S)-2-benzyloxycarbonylamino-3-[4-(5H-dibenzo[a,d]cyclohepten-5-ylidene)piperidin-1-yl] propionic acid (1.0 g,2 mmol) and triethylamine (0.2 g, 2 mmol) in 20 ml dry CH$_2$Cl$_2$ was cooled to 0° C. on a salt-ice bath. To this solution was added dropwise 0.22 g (2 mmol) of ethyl chloroformate in 5 ml dry CH$_2$Cl$_2$. After the mixture was stirred at 0° C. for 30 min., a solution of glycine ethyl ester hydrochloride (0.28 g, 2 mmol) and triethylamine (0.2 g, 2 mmol) in 10 ml dry ether was added and the mixture was stirred at 0° C. for another 30 min. The mixture was consequently stirred at room temperature for 15 min. and refluxed for 30 min. After cooling, the solution was washed with saline and organic layer was separeted, dried over Na$_2$SO$_4$ and evaporated to dryness. The oily residue was put on a silica gel column and eluated with a mixture of petroleum ether (40°–60° C.)/EtAc 1:1. To the oily residue was added a solution of oxalic acid in ether to afford the title compound as a white crystalline oxalate. Yield: 0.83 g (71%).

mp. 95.0°–97.6° C.

$[\alpha]D^{25}$–7.9°(c=1, DMF).

$^1$H NMR(CDCl$_3$)δ(ppm):1.3(t, 3H, J=6.7 Hz, CH$_2$C$\underline{H}_3$), 2.2–2.9(m, 10H,piperidine H+piperidine-NC$\underline{H}_2$CH), 3.95 (m, 1H, piperidine-NCH$_2$C$\underline{H}$), 4.15(m, 2H, CONHC$\underline{H}_2$), 4.2(q, 2H, J=6.7 Hz, C$\underline{H}_2$CH$_3$), 5.1(s, 2H, OCH$_2$Ph), 5.95(br s, 1H, NHCOO), 6.9(s, 2H, dibenzocyclohepten C$_{10,11}$—H), 7.15–7.35(m, 13H, aromatic H), 8.9(br s, 1H, CO NHCH$_2$).

Example 12

Ethyl α-{(S)-2-benzyloxycarbonylamino-3-[4-(10,11-dihydro-5H-dibenzo[a,d]cyclohepten-5-ylidene)piperidin-1-yl]propionylamino}-acetate The title compound, a white crystalline, was prepared in a similar way as described under Example 11 from (S)-2-benzyloxycarbonylamino-3-[4-(10,11-dihydro-5H-dibenzo[a,d]-cyclohepten-5-ylidene)piperidin-1-yl]propionic acid. Yield:58% mp. 125.6°–126.4° C.

$[\alpha]D^{25}$–1.0°(c=1, CHCl$_3$).

$^1$H NMR(CDC$_3$)δ(ppm):1.25(t, 3H, J=6.7 Hz, CH$_2$C$\underline{H}_3$), 2.35(m, 6H, piperidine H+C$\underline{H}_2$CHNH), 2.65(m, 4H, piperidine H), 2.8 and 3.35 (two m, each 2H, dibenzocyclohepten C$_{10,11}$—H), 3.95(d, 2H, J=7 Hz, CONHC$\underline{H}_2$), 4.15(q, 2H, J=6.7 Hz, C$\underline{H}_2$CH$_3$), 4.25 (m, 1H, CH$_2$C$\underline{H}$NH), 5.1(s, 2H, CH$_2$Ph), 5.7(br s, 1H, CH$_2$CHN$\underline{H}$), 5.85 (br s, 1H, CON$\underline{H}$CH$_2$), 7.05–7.3(m, 13H, aromatic H).

Example 13

α-{(S)-2-Amino-3-[4-(5H-dibenzo[a,d]cyclohepten-5-ylidene)-piperidin-1-yl]propionylamino}acetic acid To a solution of ethyl α-{(S)-2-benzyloxycarbonylamino-3-[4-(5H-dibenzo[a,d]cyclohepten-5-ylidene)piperidin-1-yl]propionylamino}acetate(1 g, 1.7 mmol) in 20 ml ethanol was added 20 ml of 1N NaOH solution. The mixture was stirred at room temperature for 3 hours and acidified with conc. HCl. The mixture was stirred at room temperature for another hour. After neutrallization with NaHCO$_3$, the white precipitate was collected by filtration and dried in vacuum. Recrystallization from methanol afforded the title compound as a white crystalline. Yield: 0.5 g (69%).

mp. 175.3°–176.2° C.

$[\alpha]D^{25}$–8.9°(c=1, DMF).

$^1$H NMR(DMSO-d6)δ(ppm):2.05–2.8(m, 10H, piperidine H+piperidine-NC$\underline{H}_2$CH), 3.2(s,2H,NH$_2$), 3.7(d,2H,J=5.5 Hz, CONHC$\underline{H}_2$), 4.15(m, 1H,piperidine-NCH$_2$C$\underline{H}$), 6.45(d, 1H,J=5.5 Hz, CON$\underline{H}$CH$_2$), 6.55(br s, 1H,piperidine-N$^+$H), 7.0(s,2H, dibenzocyclohepten C$_{10,11}$—H), 7.2–7.4(m, 8H,aromatic H).

Example 14

α{(S)-2-amino-3-[4-(10,11-dihydro-5H-dibenzo[a,d]cyclhepten-5-ylidene)piperidine-1-yl]propionylamino}acetic acid The title compound was prepared in a similar way as described under Example 13 from Ethyl α{(S)-2-benzyloxycarbonylamino-3-4-(10,11-dihydro-5H-dibenzo[a,d]cycloheptene-5-ylidene)piperidine-1-yl]propionylamino}acetate. Yield: 67%.

mp. 163.2°–163.4° C. $^1$HNMR(CDCl$_3$)δ(ppm):2.2(m,6H, piperidine H+C$\underline{H}_2$CHNH), 2.5 (m, 4H, piperidine H), 2.75 and 3.30 (two m, each 2H, dibenzocyclohepten C$_{10,11}$—H), 3.72(m,2H,CONHC$\underline{H}_2$), 4.15(m, 1H, CH$_2$C$\underline{H}$NH), 5.05(s, 2H,PhC$\underline{H}_2$), 6.1 and 6.3 (br, each 1H, NH), 6.8–7.15(m, 13 H, aromatic H).

Example 15

Methyl (S)-4-benzyloxycarbonylamino-4-[4-(5H-dibenzo[a,d]cyclohepten-5-ylidene)-1-piperidinocarbonyl]butyrate To a solution of γ-methyl-N-benzyloxycarbonyl-L-glutamate (3.25 g, 11 mmol) and triethylamine (1.11 g, 11 mmol) in 25 ml dry CHCl$_3$ at 0° C. was added 1.19 g (11 mmol) of ethyl chloroformate with stirring. After addition, the mixture was stirred at 0° C. for another 30 min. The obtained suspension was then added slowly to a solution of 4-(5H-dibenzo[a,d]cyclohepten-5-ylidene)piperidine(3 g, 11 mmol) and triethylamine (1.11 g, 11 mmol) in 25 ml dry CHCl$_3$. After addition, the solution was stirred at room temperature for 30 min. and then refluxed for 20 min. After cooling, the mixture was washed with H$_2$O, 0.5M NaHCO$_3$ and H$_2$O again. The CHCl$_3$ solution was dried over Na$_2$SO$_4$ and evaporated to dryness. Further purification on a silica gel column, eluated with a mixture of diethyl ether/ petroleum ether (40°–60° C.) 4:1.5, afforded the title compound as a white crystalline. Yield: 3.63 g (60%).

mp. 67.6°–68.6° C.

$^1$H NMR(CDCl$_3$)δ(ppm):1.54(m, 2H, CH$\underline{CH_2}$CH$_2$), 2.25 (m, 4H, piperidine C$_{3',5'}$—H), 3.0 and 3.6(two m, each 2H, piperidine C$_{2',6'}$—H), 3.55(s, 3H, OCH$_3$), 3.85(t, 2H, J=6.7 Hz, CHCH$_2$$\underline{CH_2}$), 4.65(m, 1H, $\underline{CH}$CH$_2$CH$_2$), 5.02(s, 2H, PhCH$_2$), 5.7(br s, 1H, NH), 6.85(s, 2H, dibenzocyclohepten C$_{10,11}$—H), 7.15–7.3(m, 13H, aromatic H).

Example 16

(S)-4-Benzyloxycarbonylamino-4-[4-(5H-dibenzo[a,d] cyclohepten-5-ylidene)-1-piperidinocarbonyl]butanoic acid A solution of methyl (S)-4-benzyloxycarbonylamino-4-[4-(5H-dibenzo[a,d]cyclohepten-5-ylidene)-1-piperidinocarbonyl]-butyrate(1 g, 1.8 mmol) in a mixture of 20 ml methanol and 5 ml 1N NaOH aquaous solution was stirred at room temperature for 2 hours. After evaporating methanol in vacuum, the solution was neutralized with 1N HCl and etracted with CHCl$_3$. After evaporating CHCl$_3$, the residue was co-evaporated twice with 50 ml toluene. The title compound was obtained as a white solid after cooling. Yield: 100% mp. 101.3°–104.1° C.

$^1$H NMR(CDCl$_3$δ(ppm):2.23–2.33(m, 6H, piperidine C$_{3',5'}$—H+CH$\underline{CH_2}$CH$_2$), 3.0 and 3.6 (two m, each 2H, piperidine C$_{2',6'}$—H), 3.95(m, 2H, CHCH$_2$$\underline{CH_2}$), 4.7(m, 1H, $\underline{CH}$CH$_2$CH$_2$), 5.05 (s, 2H, PhCH$_2$), 6.09(br s, 1H, NH), 6.89(s, 2H, dibenzocyclohepten C$_{10,11}$—H), 7.13–7.29(m, 13H, aromatic H).

Example 17

Methyl (S)-4-amino-4-[4-(5H-dibenzo[a,d]cyclohepten-5-ylidene)-1-piperidinocarbonyl]butyrate hydrobromide To a solution of methyl (S)-4-Benzyloxycarbonylamino-4-[4-(5H-dibenzo[a,d]cyclohepten-5-ylidene)-1-piperidinocarbonyl]butyrate (2.5 g, 4.5 mmol) in 25 ml of 4:1 mixture of methanol/acetic acid was added 0.5 g Pd—C (5%). The mixture was stirred at room temperature while a steady stream of N$_2$ was bubbled through. After 10 min, H$_2$ was inletted and the mixture was stirred at room temperature for another 2 hours. After filtration, the filtrate was evaporated in vacuum to remove methanol. To the residue was added an ether solution HBr and the white precipitate was collected by filtration. Recrystallization from methanol afofrded the title compound as a white crystalline. Yield:1.25 g (56%)

mp. 138.6°–140.6° C.

$^1$H NMR(DMSO-d6)δ(ppm):1.91(m, 2H, CH$\underline{CH_2}$CH$_2$), 2.0 and 2.35 (two m, each 4H, piperidine H), 3.54 (t, 2H, J=6.7 Hz, CHCH$_2$$\underline{CH_2}$), 3.56(s, 3H, OCH$_3$), 4.35(m, 1H, CHCH$_2$CH$_2$), 6.99(s, 2H, dibenzocyclohepten C$_{10,11}$—H), 7.1–7.4(m, 8H, aromatic H), 8.45(br s, 3H, N$^+$H$_3$).

Example 18

(S)-2-Amino-3-[4-(10,11-dihydro-5H-dibenzo[a,d] cyclohepten-5-ylidene)piperidine-1-yl]propionic acid The title compound was prepared from (S)-2-benzyloxycarbonylamino-3-[4-(10,11-dihydro-5H-dibenzo [a,d]-cyclohepten-5-ylidene)piperidine-1-yl]propionic acid in a similar way as described under Example 17. Yield: 83%.

mp. 150.4°–151.2° C.

$^1$H-NMR(CDCl$_3$)δ(ppm): 2.85(m, 8H, piperidine 4H+ $\underline{CH_2}$CHNH$_2$+2H from C$_{10,11}$ of dibenzocyclohepten ring), 3.40(m, 6H, piperidine 4H+2H from C$_{10,11}$ of dibenozcyclohepten ring), 4.4(m, 1H, CH$_2$$\underline{CH}$NH$_2$), 5.05(br d, J=13.5 Hz, 2H, NH$_2$), 7.1–7.3(m, 8H, aromatic H).

Example 19

Methyl (S)-4-(2-benzyloxycarbonylaminoacetamido)-4-[4-(5H-dibenzo[a,d]cyclohepten-5-ylidene)-1-piperidinocarbonyl]-butyrate To a solution of methyl (S)-4-amino-4-[4-(5H-dibenzo[a,d]cyclohepten-5-ylidene)-1-piperidinocarbonyl]butyrate hydrobromide(1 g, 2 mmol) and triethylamine(0.75 g, 7.4 mmol) in 10 ml dry CHCl$_3$ was added a solution of N-benzyloxycarbonylglycine chloride (1.68 g, 7.4 mmol) in 10 ml dry ether. After addition, the mixture was stirred at room temperature for 2 hours. The mixture was then washed with H$_2$O, 0.5M NaHCO$_3$ aqueous solution and dried over Na$_2$SO$_4$. After evaporating to dryness, the residue was put on a silica gel column and eluated with a mixture of ether/ethyl acetate 1:1 to afford the title compound as a white solid. Yield: 0.6 g (52%).

mp. 73.2°–74.4° C. $^1$H NMR(CDCl$_3$)δ(ppm): 1.7(m, 2H, CH$\underline{CH_2}$CH$_2$), 2.31(m, 8H, piperidine H), 3.34(m, 2H, CHCH$_2$$\underline{CH_2}$), 3.61(s, 3H, OCH$_3$), 3.88(m, 2H, CO $\underline{CO_2}$NH), 4.97(m, 1H, $\underline{CH}$CH$_2$CH$_2$), 5.1(s, 2H, PhCH$_2$), 5.44(br s,1H, COCH$_2$$\underline{NH}$), 6.89(s, 2H, dibenzocyclohepten C$_{10,11}$—H), 7.02–7.32(m, 14H, aromatic H+CH$\underline{NH}$CO).

Example 20

(S)-4-Amino-4-[4-(5H-dibenzo[a,d]cyclohepten-5-ylidene)-1-piperidinocarbonyl]butanoic acid hydrobromide The title compound, a white crystalline, was prepared from (S)-4-benzyloxycarbonylamino-4-[4-(5H-dibenzo[a,d] cyclohepten-5-ylidene)-1-piperidinocarbonyl]butanoic acid in a similar way as described under Example 17. Yield: 36%.

mp. 165.4°–167.3° C.

$^1$H NMR(DMSO-d6)δ(ppm): 1.89(m, 2H, CH$\underline{CH_2}$CH$_2$), 2.28(m, 4H, piperidine C$_{3',5'}$—H), 2.78 and 3.31(two m, each 2H, piperidine C$_{2',6'}$—H), 3.78(m, 2H, CHCH$_2$$\underline{CH_2}$), 4.12(m, 1H, $\underline{CH}$CH$_2$CH2), 5.7(br s, 3H, N$^+$H$_3$), 7.06(s, 2H, dibenzocyclohepten C$_{10,11}$—H), 7.15(m, 8H, aromatic H).

Example 21

(S)-4-(2-Benzyloxycarbonylaminoacetamido)-4-[4-(5H-dibenzo[a,d]-cyclohepten-5-ylidene)-1-piperidinocarbonyl] butanoic acid The title compound, a white crystalline, was prepared from methyl (S)-4-(2-benzyloxycarbonylaminoacetamido)-4-[4-(5H-dibenzo[a,d]-cyclohepten-5-ylidene)-1-piperidinoarbonyl]butyrate in a similar way as described under Example 16. Yield: 90%.

mp. 92.2°–93.0° C.

$^1$H NMR(CDCl$_3$)δ(ppm):1.9(m, 2H, CH$\underline{CH_2}$CH$_2$), 2.33 (m, 4H, piperidine C3',5'-H), 3.0 and 3.35(two m, each 2H, piperidine C2',6'-H), 3.85(m, 5H, $\underline{CH}$CH$_2$$\underline{CH_2}$+CO$\underline{CH_2}$NH), 5.08(s, 2H, PhCH$_2$), 5.85(br s, 1H, COCH$_2$NH), 6.88(s, 2H, dibenzocyclohepten C$_{10,11}$—H), 7.01–7.3 (m, 14H, aromatic H+CH$\underline{NH}$CO).

Example 22

1-(2-Benzyloxycarbonylaminoacetyl)-4-(5H-dibenzo[a,d]cyclohepten-5-ylidene)piperidine The title compound, a white crystalline, was prepared by acylation of 4-(5H-dibenzo[a,d]cyclohepten-5-ylidene)piperidine with N-benzyloxycarbonylglycine chloride in a similar way as described under Example 19. Yield: 61% mp. 142.5°–143.6° C.

$^1$H NMR(CDCl$_3$)δ(ppm): 2.25(m, 4H, piperidine C$_{3',5'}$—H), 3.0 and 3.4(two m, each 2H, piperidine C$_{2',6'}$—H), 3.95(m, 2H, CO$\underline{CH_2}$NH), 5.1(s, 2H, PhCH$_2$), 5.85(br s, 1H, COCH$_2$$\underline{NH}$), 6.9(s, 2H, dibenzocyclohepten C$_{10,11}$—H), 7.15–7.3(m, 13H, aromatic H).

Example 23

(S)-3-Benzyloxycarbonylamino-3-[4-(5H-dibenzo[a,d]cyclohepten-5-ylidene)-1-piperidinocarbonyl]propanoic acid To a solution of 4-(5H-dibenzo[a,d]cyclohepten-5-ylidene)piperidine(1 g, 3.66 mmol) in 10 ml dry pyridine was added 0.92 g (3.66 mmol) of N-benzyloxycarbonylaspartic anhydride. The mixture was stirred at room temperature for 2 hours. To the mixture was then added 25 ml cold water and acidified with cold 5N HCl. The white precipitate was collected by filtration and washed well with water. Recrystllization from ethanol afforded the title compound as a white crystalline. Yield: 1.87 g (98%)

mp. 149.0°–150.7° C.

$^1$H NMR(CDCl$_3$)δ(ppm): 2.23(m, 4H, piperidine C$_{3',5'}$—H), 2.65 and 3.07(two m, each 2H piperidine C$_{2',6'}$—H), 3.75(m, 2H, CH$\underline{CH_2}$), 4.5(m, 1H, $\underline{CH}$CH$_2$), 5.06(s, 2H, PhCH$_2$), 6.03(br s, 1H, NH), 6.89(s, 2H, dibenzocyclohepten C$_{10,11}$—H), 7.15–7.3(m, 13H, aromatic H).

Example 24

(S)-3-Amino-3-[4-(5H-dibenzo[a,d]cyclohepten-5-ylidene)-1-piperidinocarbonyl]propanoic acid hydrobromide The title compound, a white crystalline, was prepared from (S)-3-benzyloxycarbonylamino-3-[4-(5H-dibnezo[a,d]cyclohepten-5-ylidene)-1-piperidinocarbonyl]propanoic acid in a similar way as described under Example 17. Yield: 75%.

mp. 175.0°–176.1° C.

$^1$H NMR(DMSO-d6)δ(ppm):2.29(m, 4H, piperidine C$_{3',5'}$—H), 2.76 and 3.32(two m, each 2H, piperidine C$_{2',6'}$—H), 3.7(m, 2H, CH$\underline{CH_2}$), 4.25(m, 1H, $\underline{CH}$CH$_2$), 7.05 (s, 2H, dibenzocyclohepten C$_{10,11}$—H), 7.16(m, 8H, aromatic H).

Example 25

(S)-3-(2-Benzyloxycarbonylaminoacetamido)-3-[4-(5H-dibenzo[a,d]-cyclohepten-5-ylidene)-1-piperidinocarbonyl]propanoic acid The title compound, a white crystalline, was prepared from (S)-3-amino-3[4-(5H-dibenzo[a,d]cyclohepten-5-ylidene)-1-piperidinocarbonyl]propanoic acid hydrobromide in a similar way as described under Example 19. Yield: 45%.

mp. 121.0°–123.1° C.

$^1$H NMR(CDCl$_3$)δ(ppm):2.29(m, 4H, piperidine C$_{3',5'}$—H), 2.74(m, 4H,piperidine C$_{2',6'}$—H), 3.31(m, 2H, CH$\underline{CH_2}$), 3.84(m, 2H, CO$\underline{CH_2}$NH), 4.69(m, 1H, $\underline{CH}$CH$_2$), 5.0(s, 2H, PhCH$_2$), 5.2(br s, 1H, NH), 5.75(br s, 1H, COCH$_2$$\underline{NH}$), 6.96(s, 2H, dibenzocyclohepten C$_{10,11}$—H), 7.06–7.23 (m, 13H, aromatic H).

Example 26

(S)-3-(2-aminoacetamide)-3-[4-(5H-dibenzo[a,d]cyclohepten-5-ylidene)-1-piperidinocarbonyl]propionic acid The title compound was prepared in a similar way as described under Example 17 with (S)-3-(2-benzyloxycarbonylaminoacetamide)-3-[4-(5H)-dibenzo[a,d]cyclohepten-5-ylidene)-1-piperidinocarbonyl]propionic acid.

Example 27

(S)-4-(2-aminoacetamide)-4-[4-(5H-dibenzo[a,d]cycloheptene-5-ylidene)-1-piperidinocarbonyl)butanoic acid The title compound was prepared in a similar way as described under Example 17 with (S)-4-(2-benzyloxycarbonylaminoacetamide)-[4-(5H-dibenzo[a,d]cyclohepten-5-ylidene)-1-piperidinecarbonyl]butanoic acid.

Test Example 1

(1) Inhibition of histamine-or LTD$_4$-induced contraction

A piece of ileum (about 2 cm length) isolated from guinea-pigs is trimmed, tied at both ends and mounted in a 20 ml organ bath containing KREBS-buffer (37° C., constantly bubbled with 95% O$_2$-5% CO$_2$). The first three dose-response experiments are performed by adding histamine or leukotriene D$_4$ cumulatively to the organ bath. After adequate washing, the ileal strip is incubated with the testing compound for 30 min. The dose-response experiment is then conducted again. The dissociation constant (Kb) of the receptor-antagonist complex is used as the parameter to indicate the potency of the testing compound and is calculated according to the Cheng-Prusoff equation.

(2) Inhibition of [$^3$H]mepyramine binding to guinea-pig cerebellum membranes.

The method is based on that described previously. Briefly, a mixture of total volume of 1.0 ml containing 0.5 nM[$^3$H] mepyramine(specific activity 21 Ci/mmol), guinea-pig cerebellum membrane proteins(±370 µg/ml) and the testing compound in 50 mM Na—K phosphate buffer (pH 7.5) was incubated at 37° C. for 30 min. The reaction was stopped by the addition of 5 ml ice-cold phosphate buffer and followed by immediate filtration through Whatman GF/C filters. The filters were washed twice with about 20 ml cold buffer. The retained radioactivity was determined by a liquid scintillation counter after addition of 5 ml scintillation liquid.

In the saturation experiment, $10^{-4}$MR(-)dimethindene was used to define the non-specific binding. A single, saturable binding site with Bmax=278±24 fmol/mg protein was found from the saturation experiment. The $K_D$ of [$^3$H]mepyramine was found to be $3.30\pm0.26\times10^{-9}$M and no cooperativity was detected when the data were analyzed by Hill plots(slope=1.005).

(3) Inhibition of [$^3$H]LTD$_4$ binding to guinea-pig lung membranes

The method is a modification of that described in the literature*. Briefly, a mixture of total volume of 0.3 ml containing 0.2 nM[$^3$H]-LTD$_4$, guinea-pig lung membrane proteins (±170 μg/ml) and the testing compound in a 10 mM piperazine-N,N'-bis(2-ethanesulfonic) acid buffer (pH 7.5) was incubated at 22° C. for 30 min. The piperazine-N,N'-bis(2-ethanesulfonic)acid buffer contains 10 mM CaCl$_2$, 10 mM MgCl$_2$, 50 mM NaCl, 2 mM cysteine and 2 mM glycine. The reaction was terminated by the addition of 5 ml ice-cold tris-HCl/NaCl buffer (10 mM/, pH 7.5). The mixture was immediately filtered under vacuum (Whatman GF/C filters) and the filters was washed once with 20 ml ice-cold buffer. The retained radioactivity was determined by a liquid scintillation counter.

In the saturation experiment, 2 μM LTD$_4$ was used to define the non-specific binding. A single, saturable binding site with Bmax=988 fmol/mg protein was found from the saturation experiment. The Kd of [$^3$H]-LTD$_4$ was found to be $2.16\times10^{-10}$M and no cooperativity was detected when the data were analyzed by Hill plots (slope=0.99).

*D. Aharony et al: J. Pharmacol. Exp. Ther. 1987, 243, 921–926.

We claim:

1. A piperidine compound of formula (1) or a salt thereof:

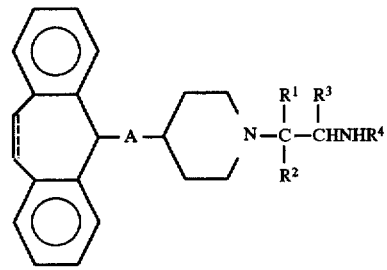

(1)

wherein $R^1$ and $R^2$ independently represent a hydrogen atom or they link to represent an oxygen atom together, $R^3$ represents a hydrogen atom, —$R^5$—COOR$^6$, or —COOR$^6$ (wherein $R^5$ is a lower alkylene group, —CONH—, or —CONHCH$_2$, and $R^6$ is a hydrogen atom or a lower alkyl group), $R^4$ represents a hydrogen atom, an aralkyloxy carbonyl group, an aminomethyl carbonyl group, or an aralkyloxy carbonyl aminomethyl carbonyl group, A represents an oxygen atom or a double bond, and the broken line has the meaning that a bonding hand may be present.

2. An antiallergic pharmaceutical composition which comprises a therapeutically effective amount of the piperidine compound as defined in claim 1 or a salt thereof and a pharmaceutically acceptable carrier.

3. The pharmaceutical composition according to claim 2, wherein said effective amount is an anti-histaminic effective amount.

4. The pharmaceutical composition according to claim 2, where in said effective amount is an anti-leukotriene effective amount.

5. A method for treating allergic diseases in a patient in need thereof, which comprises administering an anti-allergic effective amount of the piperidine compound as defined in claim 1 or a salt thereof.

TABLE 1

| drugs | activity on histamine H$_1$ receptors | | activity on leukotriene D$_4$ receptors | |
|---|---|---|---|---|
| | pA$_2$ (functional) | K$_D$ (mol/L, binding) | pA$_2$ (functional) | K$_D$ (mol/L, binding) |
| example 6 | 7.37 | $1.47\times10^{-7}$ | — | 28% inhib*$^1$ |
| example 7 | 7.48 | $8.71\times10^{-7}$ | 5.95 | $6.80\times10^{-6}$ |
| example 8 | 8.00 | $4.12\times10^{-7}$ | 6.85 | $1.55\times10^{-6}$ |
| terfenadine | 7.45 | $3.54\times10^{-7}$ | not active | not active |
| FPL55712*$^2$ | not active | not active | 6.92 | $1.12\times10^{-6}$ |

*$^1$Inhibition of [$^3$H]LTD$_4$ binding in guinea-pig receptor preparations by the drug at the concentration of $10^{-5}$ M.
*$^2$J. Med. Chem., Vol. 20, No. 3, 371–379 (1977)

As shown above, the compound (1) of the present invention has excellent antihistamine activity and antileukotriene activity, which are well balanced, and thus, they are useful for the prevention and treatment of asthma or other allergic diseases such as allergic rhinitis, dermatosis and urticaria.

6. A method of claim 5, wherein said effective amount is an anti-histaminic effective amount.

7. A method of claim 5, wherein said effective amount is an anti-leukotriene effective amount.

* * * * *